United States Patent [19]

Ellinger et al.

[11] Patent Number: 5,534,708
[45] Date of Patent: Jul. 9, 1996

[54] OPTICAL FUEL/AIR/WATER SENSOR AND DETECTOR CIRCUIT

[75] Inventors: Sylvester M. Ellinger, Charlotte; Bruce R. Kline, Starksboro, both of Vt.

[73] Assignee: Simmonds Precision Products Inc., Akron, Ohio

[21] Appl. No.: 167,742

[22] Filed: Dec. 15, 1993

[51] Int. Cl.$^6$ ........................................ G01N 15/06
[52] U.S. Cl. ...................... 250/577; 250/903; 340/619; 356/137
[58] Field of Search ................... 250/577, 900–907, 250/227.32, 227.25, 227.11; 73/293; 356/128, 133–137; 340/618, 619

[56] References Cited

U.S. PATENT DOCUMENTS

| | | | |
|---|---|---|---|
| 3,120,125 | 2/1964 | Vasel | 250/903 |
| 3,384,885 | 5/1968 | Forbush | 250/903 |
| 3,766,395 | 10/1973 | Keir | 250/214 R |
| 3,818,470 | 6/1974 | Hirsbrunner et al. | 340/244 R |
| 3,864,577 | 2/1975 | Pellett et al. | 250/577 |
| 4,155,013 | 5/1979 | Spiteri | 250/577 |
| 4,201,914 | 5/1980 | Perren | 250/341 |
| 4,242,590 | 12/1980 | von Tlück | 250/577 |
| 4,286,464 | 9/1981 | Tauber et al. | 73/293 |
| 4,354,180 | 10/1982 | Harding | 340/619 |
| 4,427,293 | 1/1984 | Harmer | 356/133 |
| 4,713,552 | 12/1987 | Denis et al. | 250/577 |
| 4,840,137 | 6/1989 | Beauvais et al. | 250/577 |
| 4,961,069 | 10/1990 | Tsaprazis | 340/619 |
| 4,998,022 | 3/1991 | Tregay | 250/577 |
| 5,048,952 | 9/1991 | Miyata et al. | 356/135 |
| 5,159,834 | 11/1992 | Eisele | 73/293 |

FOREIGN PATENT DOCUMENTS

58-26226A 2/1983 Japan.

Primary Examiner—Edward P. Westin
Assistant Examiner—Que T. Le
Attorney, Agent, or Firm—Leonard L. Lewis; Richard A. Romanchik

[57] ABSTRACT

A liquid sensing apparatus for a fuel tank comprises a first optical sensor for producing an output having a first state that corresponds to the first optical sensor being exposed to air and a second state that corresponds to the first optical sensor being exposed to fuel; a second optical sensor for producing an output having a first state that corresponds to the second optical sensor being exposed to air or water, and a second state that corresponds to the second optical sensor being exposed to fuel; and a circuit for detecting the first and second optical sensor output states. The sensor circuits can be accessed using a two wire only interface, and thermal stability can be achieved with the electronic circuit as shown.

26 Claims, 4 Drawing Sheets

CURRENT LEVELS FOR DIFFERENT INTERFACE CONDITIONS

| FIVE CONDITIONS | CURRENT (7.5 VOLTS) |
|---|---|
| AIR | 18.6ma |
| PARTIAL FUEL | 15.6ma |
| ALL FUEL | 9.5ma |
| PARTIAL WATER | 12.6ma |
| ALL WATER | 12.6ma |

OPTICAL FUEL/AIR/WATER SENSOR AND DETECTOR CIRCUIT

BACKGROUND OF THE INVENTION

The invention relates generally to optical sensors for fluids. More particularly, the invention relates to optical sensors of the type used for fluid level detection and that can discriminate different fluid types.

Optical fluid point level sensors are well known. Such sensors commonly use a prism having a conical tip. The prism is transparent to a beam of light launched into the prism from a light source (such as an LED). The light travels through the prism towards a surface of the conical tip and impinges on the surface at a determinable angle of incidence. The prism is made of a material that has a refractive index such that there exists a critical angle of incidence at which all light is internally reflected to another surface and back to a photodetector, such as a phototransistor. Whether such internal reflection occurs depends on the refractive index of the fluid to which the conical tip is exposed and the angle of incidence. The critical angle is defined by the following equation:

$$\theta_c = \sin^{-1}(n_2/n_1) \qquad \text{Eq. 1}$$

where $n_2$ is the index of refraction of the fluid, and $n_1$ is the index of refraction of the prism conical tip. Thus, for air, $n_2=1.00$ and for glass, $n_1=1.50$. Accordingly, for total internal reflection the critical angle with respect to air is about 42°. By comparison, if the conical tip is exposed to water as the fluid, the refractive index of water is 1.33. Thus the critical angle for total internal reflection with respect to water is about 62.5°.

By forming the conical surfaces such that the light transmitted therethrough is incident at 45°, the light will undergo total internal reflection (hereinafter "TIR") when the conical tip is exposed to air (because 45° is greater than the critical angle of 42° for a glass/air interface), but will not undergo TIR when the conical tip is exposed to water (because 45° is less than the critical angle of 62.5° for a glass/water interface). By positioning a light detector to receive the light that is internally reflected, the prism can be used as a point level detector for the water level. The transmitted light that is not internally reflected is refracted into the fluid, as is well known.

Note that for TIR to occur, the refractive index of the conical tip is higher than the refractive index of all fluids which are to be detected (in this example, air and water).

Such a prismatic sensor can also be used to detect an aircraft fuel/air interface when the prism material is made of a higher refractive index such as 1.65, because the index of refraction for fuel is on the order of 1.4 to 1.5. Thus, it is known to use such sensors for fuel level detection by detecting the ullage/fuel interface at different levels in a fuel tank.

A significant problem in aircraft fuel tanks, particularly large commercial aircraft flying at high altitudes for extended periods of time, is the accumulation of free water at the bottom of the tank. This free water can adversely affect the performance of capacitance type fuel quantity sensors; although such erratic behavior can be used as a warning that water is accumulating in the tank. Typically, tank sumps are opened to drain the water from the tanks. Most aircraft also have scavenge pumps that are used to mix the water with the fuel and burn it off prior to buildup of any significant amount.

Free water is continually being generated in the fuel tanks. During ascent, the fuel cools and water is thrown out of solution. Further, during descent, moist air is sucked into the tanks and condensation occurs on the surface of the fuel and cooled structural members.

The fuel tanks on such aircraft can remain below 0° C. for several hours after landing. As a result, the free water freezes and the scavenge pumps and sumps are ineffective. Even after refueling, the ice can remain for extended periods. Short layovers and improper fuel storage and fueling operations at remote locations can cause even more free water to be loaded on-board the aircraft.

Conventional optic fluid level sensors such as just described are ineffective in such circumstances because the prism/water interface does not cause TIR. Thus, water in the tank can be misinterpreted by such sensors as being fuel.

Optical sensors known heretofore also use three electrical conductors to access the sensor and couple the output to a fuel management system, which can add significantly to the weight of the aircraft.

Another significant drawback of known optic sensors is that the electronics housed in the each sensor tend to be very sensitive to operating temperatures and electromagnetic interference, thus requiring additional circuitry for temperature compensation and filtering.

The objectives exist, therefore, for an optical sensor for fuel level sensing that can discriminate between air, fuel and water. Such a sensor should also be able to detect ice as well as liquid water, and preferably should exhibit stable operation over a wide operating temperature range. Furthermore, such a sensor should use a minimal number of conductors for interfacing to control circuitry.

SUMMARY OF THE INVENTION

To the accomplishment of the aforementioned objectives, the present invention contemplates, in one embodiment, a liquid sensing apparatus for a fuel tank comprising: a first optical means for producing an output having a first state that corresponds to the first optical means being exposed to air and a second state that corresponds to the first optical means being exposed to fuel; second optical means for producing an output having a first state that corresponds to the second optical means being exposed to air or water, and a second state that corresponds to the second optical means being exposed to fuel; and circuit means for determining said first and second optical means output states.

The invention also contemplates an optic sensor that can discriminate between air and water in one mode, and fuel in another mode; one embodiment of such a sensor being an optical detector for discriminating between air or water and aircraft fuel comprising: a prism with a frusto-conical tip that receives light from a light source and internally reflects light to a light detector when said tip is exposed to air or water, and refracts light into fuel when said tip is exposed to fuel, said prism comprising polyethersulfone.

The invention also contemplates, in another embodiment, an electronic circuit for interrogating an optical sensor, wherein such a circuit comprises power source means for applying voltage to the light source, and means for detecting the light receptor switch state based on current drawn from said power source means, said electronic circuit being connected to the optical detector by not more than two wires.

The present invention also contemplates the methods of use embodied in such apparatus and devices, as well as a method for liquid detection in a fuel tank, comprising the steps of: a) using a first prism to internally reflect light from a light source to a light detector when the prism is exposed to air, and refracting light away from the detector when the prism is exposed to fuel; and b) using a second prism to internally reflect light from a light source to a light detector when the second prism is exposed to water, and refracting light away from the detector when the second prism is exposed to fuel.

These and other aspects and advantages of the present invention will be readily understood and appreciated by those skilled in the art from the following detailed description of the preferred embodiments with the best mode contemplated for practicing the invention in view of the accompanying drawings.

DETAILED DESCRIPTION OF THE INVENTION

Figure 1:
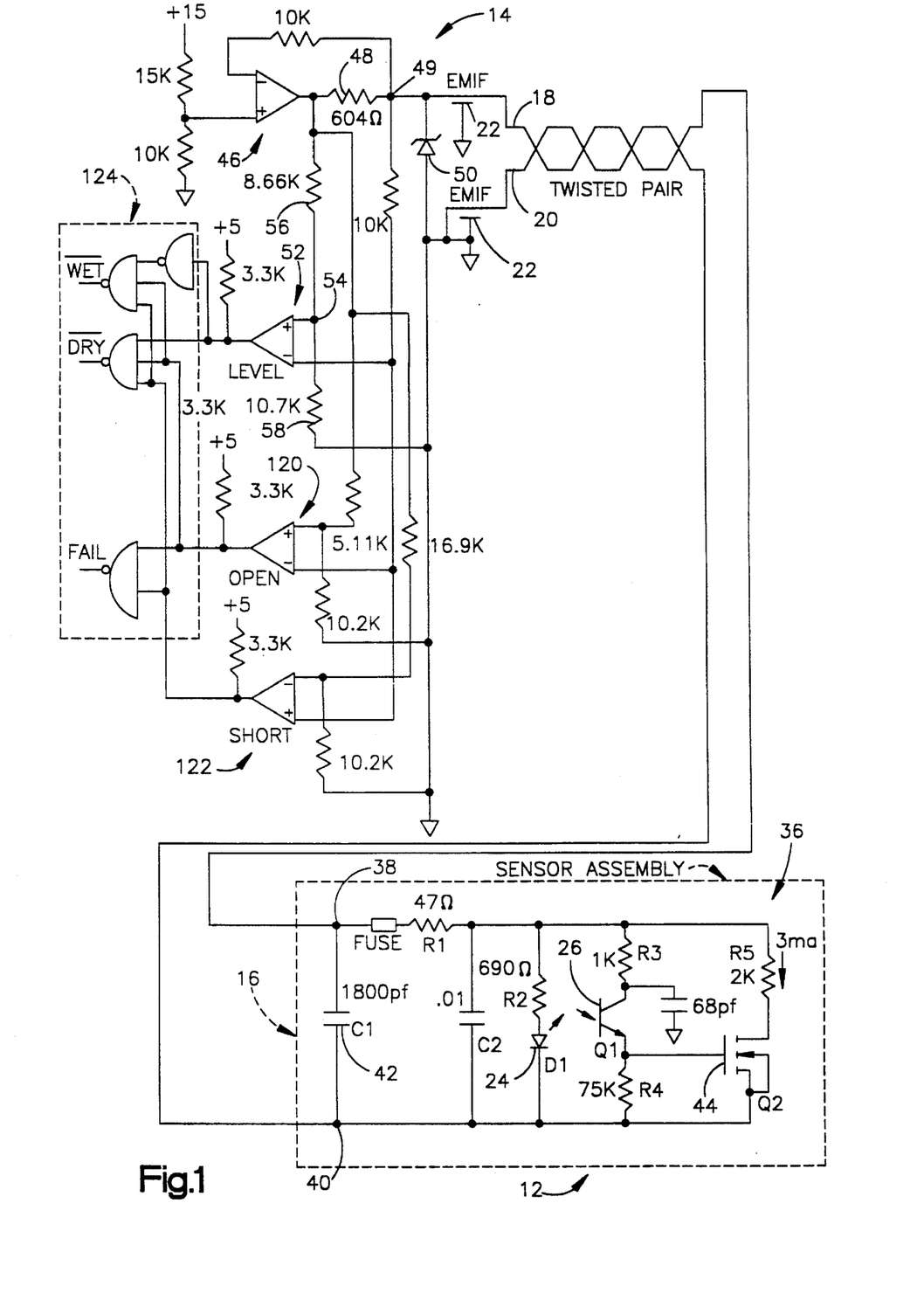
FIG. 1 is an electrical schematic diagram of an optical point level fuel sensor and a circuit for interrogating such a sensor, in accordance with the present invention.
Figure 2A:
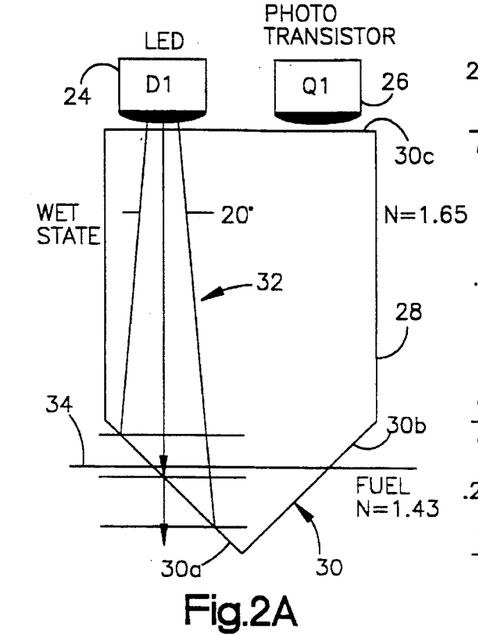
FIGS. 2A and 2B are simplified schematic drawings of an air/fuel optic sensor suitable for use with the apparatus of FIG. 1.
Figure 2B:
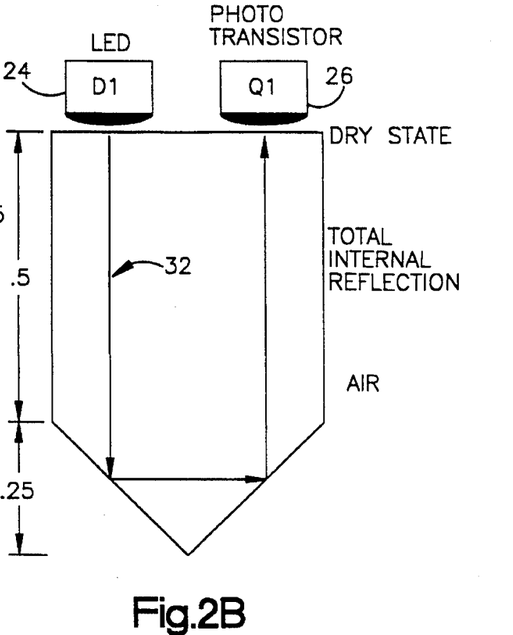

With reference to FIGS. 1, 2A and 2B, a first embodiment of an optic point level sensing apparatus for fluid in a tank is generally designated with the numeral 10. Such apparatus is particularly well suited for detecting fuel levels in an aircraft fuel tank. Although the invention is described herein with particular reference to its use in aircraft fuel tank applications, such description is intended to be exemplary and should not be construed in a limiting sense. Those skilled in the art will readily appreciate that the advantages and benefits of the invention, as will be apparent from the following description, can be realized in other applications as well.

The apparatus 10 includes an optic sensor assembly 12, and a detector circuit 14 that is used to energize the sensor 12 and determine the sensor output conditions. In the embodiment of FIG. 1, all of the components associated with the sensor 12 (as enclosed by the box designated "sensor assembly") can conveniently be disposed in a single housing 16. In accordance with one aspect of the invention, it will be noted that only two wires or conductors 18,20 are needed to connect the circuit 14 to the sensor 16 circuitry. As represented in FIG. 1, these wires can be arranged as a twisted pair to reduce sensitivity to electromagnetic interference (EMI). The two wires 18,20 are used both for coupling electrical energy to the sensor 12, as well as to couple data or signals corresponding to the sensor output back to the circuit 14. Noise on the twisted pair can be suppressed by the use of EMI filters 22, such as part no. 1270-016 available from Murata.

The sensor assembly 12 is disposed in a liquid tank, such as an aircraft fuel tank (not shown), such as by mounting the housing 16 on the bottom of the tank, for example. The detector circuit 14 can be remotely located with other electronic equipment of the aircraft, such as the fuel management electronics.

One embodiment of the optical elements of the sensor assembly 12 is shown in a simplified manner in FIGS. 2A and 2B. The sensor 12 includes a light source 24, such as an LED, and a light detector 26 such as a phototransistor. Attached to the housing 16 (not shown in FIG. 2A, B) is a prism 28 that includes the aforementioned 45° conic tip 30. The sensor 12 in this case is designed to discriminate air and fuel so that the point level of the fuel/air interface in a fuel tank can be determined. Collimating lenses can be used to improve the optical coupling between the photodevices 24, 26 and the prism. The prism is preferably made of polyethersulfone, available under the tradename RADEL A from Bronze and Plastics Specialties, that has an index of refraction of about 1.65. This material has been found to be well suited for fuel tank applications as it is compatible with aircraft fuel, and has a refractive index that is higher than the refractive index of the fuel, the latter typically being about 1.43. The material has a transmissivity of about 73% at 930 nm, thus making it convenient for use with standard LED and phototransistor devices. Polyethersulfone is machinable and moldable to form the conical point 30 in a conventional manner.

The optics portion of the sensor assembly 12 operates in a straightforward manner. FIGS. 2A and 2B illustrate the principles involved for two conditions. In the condition represented in FIG. 2A, the conical point 30 is exposed to fuel (or stated more generally, to a fluid having a refractive index higher than air but less than the prism). The LED 24 emits a beam of light 32 such that the beam is incident on a first surface 30a at an angle of about 45°. Because the critical angle for the fuel/prism interface is greater than 45°, most of the light from the incident beam 32 is refracted into the fuel. Preferably, the transmitted beam 32 has a beam width or spread (in FIG. 2A this angle is shown to be about 20°), some of the light incident on the first surface 30a may be reflected to a second surface 30b of the conical tip 30, at which point it will then pass into the fuel. Essentially no light, or very little light, returns to the phototransistor 26. In accordance with one aspect of the invention, using a transmitted light beam with a beam spread such as 20°, in this case, reduces the sensitivity of the sensor 12 to residual fuel droplets that might adhere to the conical surfaces. Other beam spreads, such as 10° for example, may also be suitable, depending on the particular application. When the light source is an LED, the beam spread can be selected by the designer based on the device selected, such as a device that includes a lens to provide the desired beam spread, as is well known to those skilled in the art.

The LED and phototransistor are arranged in the housing 16 such that there is good optical coupling between the photodevices and the prism. For example, the prism surface 30c that is adjacent the photodevices can be polished, and the photodevices mounted near this surface.

In the case of FIG. 2B, the conical tip is exposed to air. Because the critical angle for the air/prism interface is less than 45°, virtually all of the transmitted light beam 32 is internally reflected back to the phototransistor 26 due to TIR, as represented diagrammatically by the arrows in FIG.

2B. Therefore, the point level of the fuel surface 34 can be detected by monitoring the operation of the phototransistor 26.

With reference again to FIG. 1, from an electrical point of view, the LED 24 and phototransistor 26 are part of a sensor circuit 36 that can be interrogated by the detector circuit 14. In accordance with anther aspect of the invention, the sensor circuit 36 can be accessed by remote electronics, such as the detector circuit 14, by a simple two wire connection. This is accomplished, in general, by having the sensor circuit 36 configured as a variable current load that varies as a function of the on/off state of the phototransistor 26.

The wires 18,20 can be connected to the sensor circuit at input terminal nodes 38,40 respectively.

A noise suppression capacitor 42 is provided across the input nodes 38,40 for enhanced noise immunity. The LED (D1) 24 is connected in series with a first resistor R2 across the terminals 38,40. The R2 resistor limits the current flow through the forward biased diode 24 when the diode is emitting light. In this example, the value of R2 is selected such that the forward bias current through the diode 24 is about 7 ma (assuming a bias voltage across the input nodes 38, 40 of about 6 volts).

The phototransistor 26 is connected in series with a collector resistor R3 and an emitter resistor R4 between the input nodes 38, 40. A MOSFET transistor 44 is configured as a switch to increase load current of the circuit 36 when the phototransistor 26 turns on. The value of the resistor R4 is selected so that when the phototransistor 26 is off (corresponding to a wet state of the conical tip 30, as in FIG. 2A, for example), the FET 44 gate voltage is below the gate-source threshold voltage, and the FET device is off.

When the phototransistor 26 turns on (corresponding to a dry state of the conical tip 30, as in FIG. 2B, for example), the phototransistor produces an output current of about 300–400 μa. This current is sufficient to produce a voltage across resistor R4 that exceeds the gate-source threshold voltage of the FET 44, thus turning the FET on. The FET turns on under these conditions and draws about 3 ma (for a 6 volt bias voltage across the nodes 38,40), so that the total load of the sensor circuit increases to about 10 ma.

The 3 ma differential load current that is produced by the sensor circuit 12 between the wet and dry states is detected by the detector circuit 14. The detector circuit 14 produces an output signal that indicates the wet/dry state of the sensor assembly.

The detector circuit 14, in the embodiment of FIG. 1, includes a constant voltage source 46, realized in the form of an operational amplifier configured as a voltage follower in a known manner. A current sense resistor 48 is connected in series between the amplifier output of the voltage source 46, and a node 49 that is connected to the positive input node 38 of the sensor circuit 36 by one of the wires 18 of the twisted pair. The voltage at node 49 is a fixed reference voltage by operation of the voltage source 46. A zener diode 50 is used to prevent over voltage due to lightening strikes or short circuits.

The detector circuit also includes a comparator circuit 52. The non-inverting input (+) of the comparator 52 is connected to a resistor divider node 54 at the junction of two bias resistors 56,58. The inverting (−) input to the comparator 52 is connected to the fixed voltage side of the current sensing resistor 48. The resistors 56,58 are selected such that the comparator 52 threshold is nominally symmetrical about the constant voltage source output at node 49. Small value capacitors (not shown) could be included at the comparator 52 inputs to reduce sensitivity to fuel sloshing or short electrical transients, however, their use is not required. Note that the detector circuit 14 as configured in FIG. 1 compensates for variations in the constant voltage source output at node 38.

The circuit 14 includes two additional comparator circuits 120 and 122. The comparator 120 is used for an open circuit condition self-test, and the comparator 122 is used for a short circuit condition self-test. Note that the self-test comparators can be used with a detector circuit such as shown and described with respect to FIG. 6.

The open circuit test is accomplished by appropriate biasing of the comparator 120. As stated, the sensor circuit 36 has a minimum load current, in this case about 7 ma. Therefore, the comparator 120 is configured to monitor the voltage across the current sense resistor 48 and to change state from high to low if the load current falls below a defined tolerance, for example, 5 ma. The tolerance can be set as a function of the expected worst case load current condition for the photodiode 24. An excessively low load current would be an indication of a possible open circuit or similar fault in the twisted pair 18,20 or the sensor circuit.

The short circuit test is accomplished by appropriate biasing of the comparator 122. As stated, the sensor circuit 36 has a load current that at its maximum can be defined by the current drawn by the photodiode 24 and the switching FET 44. For the sensor circuit in FIG. 1, this load current maximum is about 10 ma. Therefore, the comparator 122 is configured to monitor the voltage across the current sense resistor 48 and to change state from high to low if the load current exceeds a defined tolerance, for example, 15 ma. The tolerance can be set as a function of the expected worst case load current condition for the photodiode and MOSFET switch.

The detector circuit 14 further can include a series of logic gates 124 configured as shown that logically combine the outputs of the various comparators 52,120 and 122 to produce outputs that indicate the self-test functions and the sensor outputs.

When the sensor 12 is "wet", the load current of the sensor circuit 36 is about 7 ma, as described, and in the "dry" state is about 10 ma. The current sense resistor 48 is selected such that, at a load current of 7 ma (wet sensor), the output of the comparator 52 is logic low because the non-inverting input is biased below the inverting input; and when the load current is 10 ma (dry sensor), the output of the comparator 52 is logic high because the non-inverting input voltage increases above the inverting input due to the effect of the increased load current. Thus, the detector circuit 14 provides an output signal (logic high and low) that corresponds to the optical output of the sensor 12 (TIR and no TIR).

For the described embodiments, a suitable LED device is part no. SEB455-003 available from Honeywell, and a suitable phototransistor is part no. SD5443-003 also available from Honeywell. A suitable device for the MOSFET 44 is part no. JANTX2N6661 available from Motorola. Other exemplary component values are provided in the schematics of the various Figures herein, and it will be understood that these values will be selected depending on the particular application.

In accordance with another aspect of the invention, the sensor circuit design has inherent temperature stability. As is known, the photodevices 24,26 exhibit considerable temperature sensitivity, and in particular, the LED power degrades as temperature increases, and the output current of the phototransistor increases with temperature. However, the FET 44 also is temperature sensitive, with the threshold voltage increasing with temperature. The FET and phototransistor changes with temperature tend to offset the possible degraded performance of the LED with temperature. The net effect of all three devices changing with temperature is that the performance of the sensor circuit is less affected by wide changes in operating temperature range.

The polyethersulfone conical point detector and associated circuitry is thus useful for detecting a fuel/air interface, such as for a liquid point level sensor. However, because the refractive index of water is about the same as for fuel, the 45° conical sensor design is not used to detect water in the fuel tank.

Figure 3:
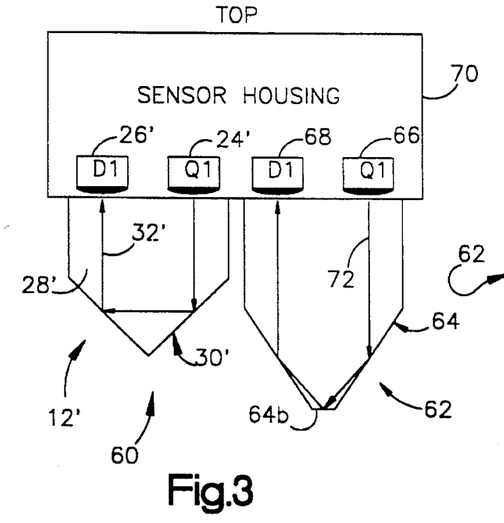
FIG. 3 is a simplified schematic of a dual prism fuel level sensor according to the invention.

In order to discriminate water from fuel, the present invention contemplates, in another embodiment, a two prism sensor apparatus 60 such as illustrated in FIGS. 3. The dual prism apparatus includes a first optical sensor 12' that can be, for example, substantially the same as the sensor 12 described hereinbefore. The sensor 12' is thus used to detect a fuel/air interface based on TIR occurring when the sensor conical tip 30' is dry, and refracting light into the fuel when the tip is wet. The sensor electronics (see FIG. 5) for the sensor 12' is substantially the same as the embodiment of FIG. 1 (except for the load current value when the FET switch turns on).

Figure 4:
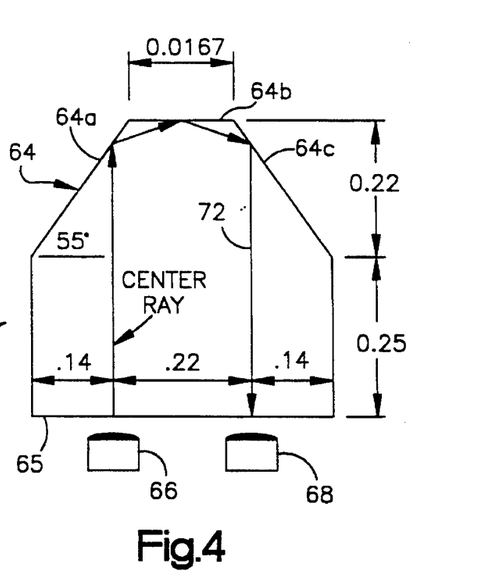
FIG. 4 is an enlarged more detailed view of a water/fuel discriminator useful with the dual prism apparatus of FIG. 3.
Figure 5:
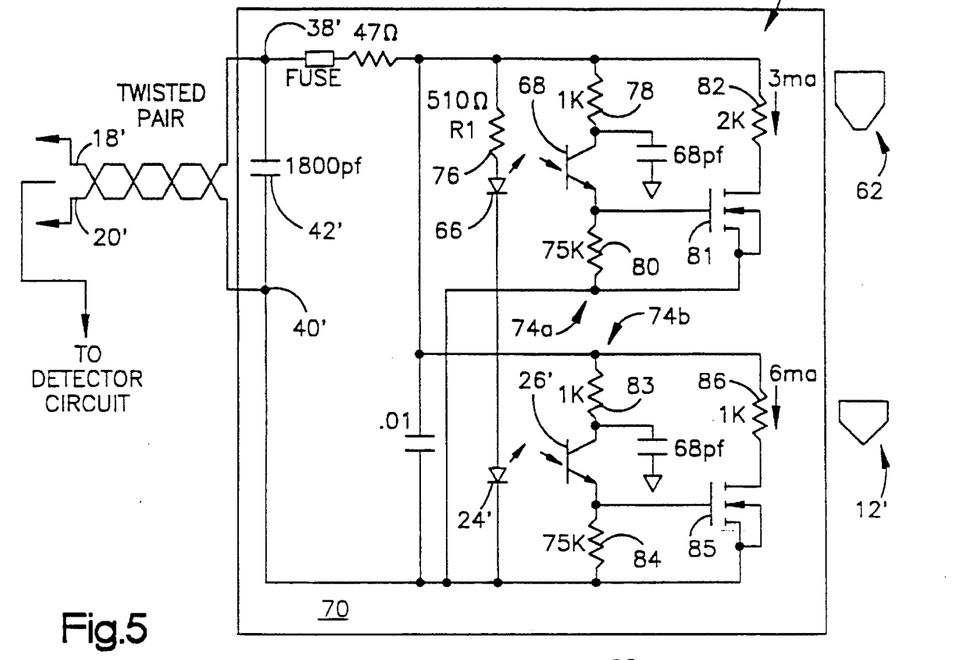
FIG. 5 is an electrical schematic diagram of a sensor circuit suitable for use with the dual prism embodiment of FIG. 3.

The apparatus 60 further includes a second optical sensor 62. Exemplary dimensions are provided in FIG. 4 (as also in FIG. 2B). This optical sensor can be used to discriminate water from fuel (and if desired, also to detect an air/fuel interface). As shown in more detail in FIG. 4, the sensor 62 is similar to the conical sensor 12', except that the tip 64 is in the form of a truncated cone or frusto-conical contour. The frusto-conical tip thus includes three reflective surfaces 64a, 64b and 64c, with the surface 64b being generally flat. An LED 66 and phototransistor 68 can be optically coupled to the truncated cone prism 64 in a manner similar to the LED and phototransistor for the conical sensor 12'. As shown in FIG. 3, the prisms can be disposed in a fuel tank by means of a housing 70 that can be mounted to a tank wall. The housing 70 also conveniently encloses the sensor 60 electronics (FIG. 5).

As shown in FIG. 3, for a top mounted apparatus 60, the air/fuel sensor 12' is axially and slightly shorter than the water/fuel sensor 62 so that it detects air before the second sensor 62. This is to avoid ambiguity at an air/fuel interface, because the second sensor 62 will also detect air in the same manner as it detects water, i.e. TIR occurs if the truncated cone is exposed to air or water. Thus, the dual prism apparatus can be used to discriminate water/fuel/air interfaces at the prism tips. If the apparatus 60 is bottom mounted, the sensor 12' would preferably be slightly longer than the sensor 62 to avoid the ambiguity.

The truncated cone prism 62 can also be formed from polyethersulfone. The conical surface is formed at an angle of 55° (with respect to the horizontal axis as viewed in FIG. 4). This produces an angle of incidence with respect to the center beam 72 of about 55°, which is greater than the critical angle for the prism when exposed to water. Therefore, TIR will occur when the truncated cone is exposed to water (or air) and light will be reflected back to the phototransistor 68. When the truncated cone is exposed to fuel, all the light essentially exits the prism 62 into the fuel. The flat surface 64b can be top cut for example with 400 grit wet/dry paper followed by 15 micron and 3 micron polishing disks. The conical surface 64a/c can be machined and vapor polished in a known manner. For optimum performance, the surface 64b should be parallel with the surface 65. The angle formed at the juncture of the surface 64b and the conical surface 64a, c should also be very acute with minimal rounding.

In accordance with the invention, the sensor 62 not only detects liquid water, but also will exhibit TIR when the water is frozen in the bottom of the fuel tank. The use of a wide beam of light, such as the 20° beam spread described hereinbefore, reduces sensitvity of the sensor 62 to ice accretion and residual fuel on the sensor tip 64. If smooth ice forms on the surface, light is reflected off of the outer surface of the ice back to the phototransistor. However, rough ice formation is more common in a fuel tank application and results in substantially less reflection. The wide beam spread helps reduce sensitivity to such ice formation. The frusto-conical sensor therefore, functions to accurately discriminate water and ice from fuel.

Although the frusto-conical sensor 62 can distinguish water from fuel, it also will provide TIR for air. Therefore, the conical sensor 12' is used to determine whether the sensor 62 is exhibiting TIR due to water or air.

With reference to FIG. 5, one embodiment of a sensor circuit 74 for the dual prism apparatus is shown. This circuit embodies similar features as the circuit 36 of FIG. 1 in that it can be accessed using a two wire only connection, and the sensors' status is detected as a function of the load current drawn by the circuit 74. Like components are identified with the same reference number followed by a prime (').

The circuit 74 thus includes two terminal nodes 38' and 40'. The LEDs 66 and 24' are connected in series with a current limiting resistor 76. When neither sensor 12', 62 exhibits TIR, the diodes 66, 24' draw about 9.5 ma current (assuming a supply voltage of about 7.5 VDC).

The truncated conical sensor circuit 74a includes phototransistor 68 connected in series with two biasing resistors 78,80 across the input nodes 38',40' as shown. A first MOSFET 81 is provided with its gate connected to the emitter of the phototransistor 68. The emitter bias resistor 80 is selected so that the FET 81 cannot turn on if the phototransistor 68 is off. A current limiting resistor 82 is series connected between the drain and the positive node 38'. The source of the FET 81 is connected to the return node 40'.

The phototransistor 26' optical output is detected by a circuit 74b that is substantially the same as the sensor circuit 36 in FIG. 1. Thus, phototransistor 26' is connected to a collector resistor 83 and an emitter resistor 84. The phototransistor emitter is also connected to the gate of a second MOSFET 85. The MOSFET drain 85 is connected to the positive input node 38' by a resistor 86.

Note that the conical sensor circuit 74b uses a 1 kohm drain resistor 86, whereas the circuit 74a uses a 2 kohm resistor (as does the corresponding circuit in FIG. 1). This is done so that the load current change caused by the second FET switch 85 turning on is twice the load current change caused by the first FET switch 81 turning on.

The circuits 74a and 74b operate in substantially the same manner as the circuit 36 in FIG. 1, except for the actual load current values. Thus, the FET switches 81,85 function to provide a load current change that represents the output state of the respective phototransistors 68, 26'.

A twisted wire pair 18', 20' can be used to connect the circuit 74 to a detector circuit illustrated in FIG. 6 and described hereinafter.

Operation of the circuit in FIG. 5 is such that four discrete load current levels are produced depending on the output states of the optical sensors 12' and 62. The circuit 74 is a two terminal circuit requiring only two wires for connection, and can be energized by a detector circuit of the configuration shown and described with respect to FIG. 6 herein. Accordingly, a voltage source is connected across the input nodes 38' and 40', such as about 7.5 volts.

Figure 7A:
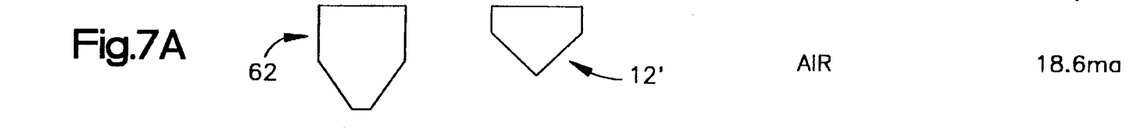
FIG. 7A–7E illustrates various exemplary operating conditions and load current levels for the embodiment of FIG. 5.

With reference to FIGS. 5 and 7, when both sensors 12' and 62 are exposed to air (as illustrated in FIG. 7A), both sensors exhibit TIR and cause maximum load current from the circuit 74. The FET switches 81, 85 are both turned on so that the total load current is approximately the sum of the current drawn by the LEDs 24', 66 (about 9.5 ma), the current drawn by the first FET 81 (about 3 ma) and the current drawn by the second FET 85 (about 6 ma). Thus, as noted in FIG. 7A the load current for both sensors exposed to air is about 18.6 ma.

Figure 7B:
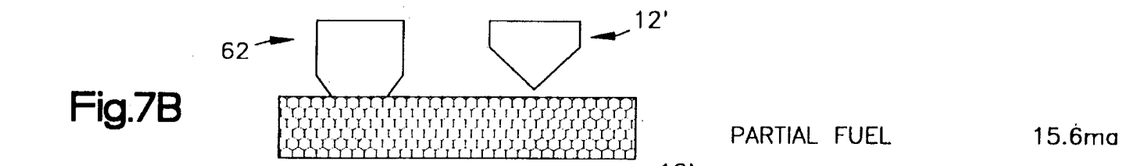

When the conical sensor 12' is exposed to air but the frusto-conical sensor 62 is exposed to fuel (FIG. 7B), the first FET switch 81 is off and the second FET switch 85 is on, thus producing a total load current of about 15.6 ma.

Figure 7C:
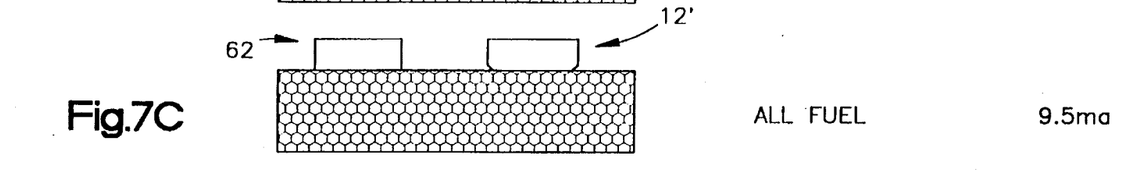

When both sensors 12', 62 are exposed to fuel (FIG. 7C), both FET switches 81, 85 are off so that the load current is at a minimum with the LEDs 66, 24' turned on, or about 9.5 ma.

Figure 7D:
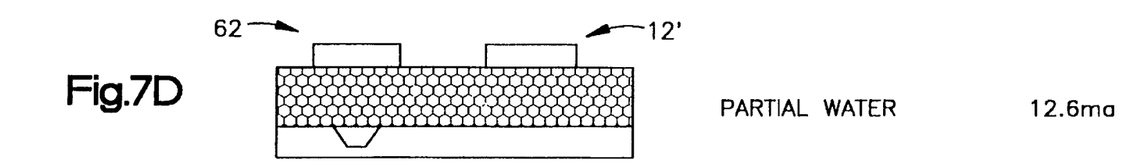

When the conical sensor 12' is exposed to fuel but the tip of the frusto-conical sensor 62 is exposed to water (FIG. 7D), the first FET switch 81 is on because the sensor 62 exhibits TIR. The second FET switch 85 is off because water causes diffraction of light through the sensor and prevents TIR. Thus, the total load current is about 12.6 ma.

Figure 7E:
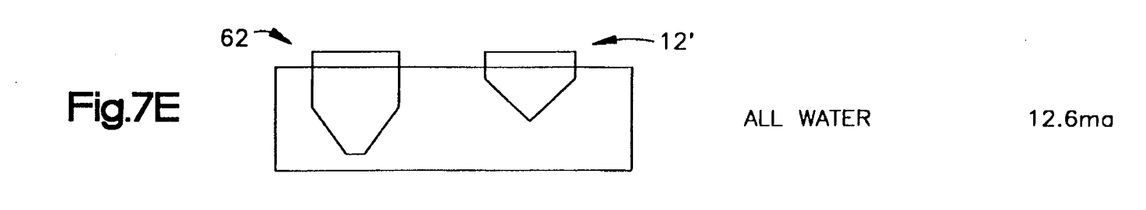

When both sensors 12', 62 are exposed to water (FIG. 7E), the load current is also 12.6 ma.

Thus, the dual sensor arrangement of FIG. 5 provides four load current levels, each of which corresponds to a unique condition so that it can be determined whether the sensors are exposed to air, fuel or water.

Figure 6:
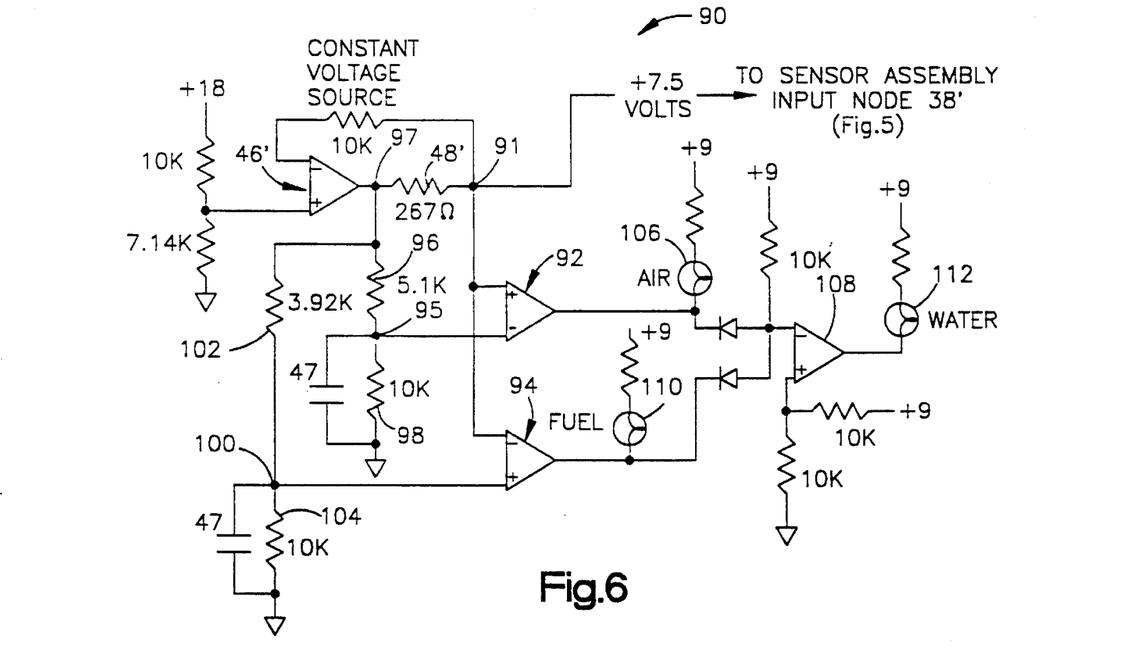
FIG. 6 is another embodiment of a detector circuit suitable for use with the present invention.

With reference now to FIG. 6, there is shown another embodiment for a detector circuit 90 that is useful to detect the discrete current loads of the circuit 74. This detector circuit 90 detects the discrete load currents of the sensor circuit 74 (FIG. 5) in a manner somewhat similar to detector circuit 14 of FIG. 1. Therefore, like reference numerals are used for like components followed by a prime (').

In accordance with the invention, the circuit 90 includes a constant voltage source 46' which, in this case, is configured to produce a 7.5 VDC fixed output at a reference node 91. This reference voltage is connected to the input node 38' of the sensor assembly circuit 74 (FIG. 5).

A load current sense resistor 48' is provided between the output 97 of the voltage source 46' amplifier and the reference node 91.

The reference voltage at node 91 is input to the non-inverting input (+) of an air/liquid comparator 92 and the inverting input (−) of a fuel/water comparator 94.

The inverting input (−) of the comparator 92 is connected to a junction node 95 of a resistor divider network that includes a first resistor 96 connected to the load current sensor resistor 48' at node 97 and a second resistor 98 connected to the return. In this manner, the inverting input of the comparator 92 will vary as a function of the load current.

In a similar manner, the non-inverting input of the comparator 94 is connected to a junction node 100 of another resistor divider network that includes a resistor 102 connected to the load current sense resistor node 97 and another resistor 104 connected to the return. Thus, the non-inverting input of the comparator 94 will vary as a function of the load current.

The resistor values for the divider network 96, 98 are selected so that the comparator 92 changes output state from high to low when the load current exceeds about 14 ma, which will occur, for example, when the conical sensor 12' is exposed to air but the frusto-conical sensor 62 is exposed to fuel. When the comparator 92 output goes low it turns on a lamp 106 that indicates the conical sensor is exposed to air.

The resistor values for the divider network 102, 104 are selected so that the comparator 94 changes output state from high to low when the load current is less than about 11 ma, which will occur, for example, when both sensors are exposed to fuel. Note that when the output of the comparator 94 is low, a lamp 110 turns on to indicate the presence of fuel.

The outputs of the comparators 92, 94 are logically combined by another comparator 108, which produces an output that indicates the presence of water. When the comparator 108 output is low, a WATER lamp 112 is turned on.

Operation of the circuit of FIG. 6 will be best understood with reference to FIG. 7. When both optical sensors 12', 62 are exposed to air (FIG. 7A), the load circuit is about 18.6 ma so that the output of comparator 92 is low (AIR lamp 106 on) and the output of comparator 94 is high (Fuel lamp 110 off). Thus, the output of comparator 108 is also high and the WATER lamp 112 is off.

When the conical sensor is exposed to air but the frusto-conical sensor is exposed to fuel (FIG. 7B), the load current is about 15.6 ma. In this case, the comparator 92 output is low (AIR lamp 106 on) and the comparator 94 output is high (FUEL lamp 110 off). Thus, the output of the comparator 108 is high and the WATER lamp 112 is off.

When both sensors are exposed to fuel (FIG. 7C), the load current is about 9.5 ma, and comparator 92 output is high (AIR lamp 106 off) and the output comparator 94 is low (FUEL lamp 110 on). The output of the comparator 108 will be high.

When the frusto-conical sensor 62 is exposed to water and the conical sensor exposed to water or fuel (FIGS. 7D and 7E), the load current is about 12.6 ma so that the output of the comparator 92 is high (AIR lamp 106 off) and the output of the comparator 94 is high (FUEL lamp 110 off). In this case, the output of the comparator 108 is low so that the WATER lamp 112 is on.

Although not shown in FIG. 6, the detector circuit 90 can be further provided with self-test capability by the use of additional comparators, as previously described with respect to FIG. 1. For example, an open circuit test could be realized by the use of a comparator arranged to detect when the load current falls below a minimum level, based on the expected worst case current drawn by the LEDS. A short circuit test could be realized by the use of another comparator that detects an excessive load current, based on the worst case load current expected when all LEDs and FET switches are on.

Those skilled in the art will further appreciate that the optical sensors can also be used in a visual sensor mode. For example, the base of the truncated cone can be visually monitored to detect for the presence of water. Ambient light that impinges on the base of the cone is reflected back to the viewer when the cone is surrounded by air or water and is dispersed when surrounded by fuel. The light at the base can either be natural light in daylight hours or from a source such as a flashlight in darkness. The difference in light contrast between water and fuel as seen by the viewer is approximately 100 to 1. The base of the cone in the presence of water appears as a donut with the sidewalls twice as bright as the flat top due to light being reflected twice off the frusto-conical surface. The cone could be screwed directly into the base or side of the tank. Commercial aircraft have an enclosed drain valve in the lowest part of the fuel tank. The cone can be mounted adjacent to the valve. The optimum prism for visual observation would have an adjacent angle of 55 degrees for polyethersulfone and a top surface diameter of 0.25 inches. The height would be determined by water depth to be sensed. The donut would encompass the complete sidewall in the optimum design.

The sensor 12 and sensor circuit 14, for example, can also be used as a direct two terminal replacement for a thermistor bead fuel level sensor. The majority of fuel level sensors in use today are thermistor beads which are biased typically at about 50 milliamperes and in the dry state have a surface temperature of about 175 degrees centigrade at an operating environment of 70 degrees. The resistance of the thermistor bead is typically 90 ohms in the wet state and 60 ohms in the dry state. The circuits described herein for the interface electronics to the conical point sensor can simulate the thermistor bead and is interchangeable with existing thermistor bead sensors.

The two terminal sensor interface is compatible with a number of detector interfaces. An important advantage of the optical sensor is the operating temperature which is a maximum of 10 degrees centigrade above the operating environment. Thermistor beads have other problems besides an operating temperature near the fuel flash point such as slow response times, procurement difficulties in as much as they are customized for the application in small production lots which makes them expensive, and limited EMI levels.

Although the invention has been described with respect to the use of the detector circuit in combination with two optical fluid level detectors (such as FIG. 5), those skilled in the art will readily appreciate that any number of optical detectors can be used in combination with the detector circuit. By simply using additional comparator circuits that are configured to detect discrete load current changes, the two wire interface can be used for a large number of optical fluid level detectors where each optical detector causes a detectable load current change based on its output condition. Thus, for example, a number of optical detectors could be used to detect fluid levels at different levels in a tank.

While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

We claim:

1. A liquid sensing apparatus for a fuel tank comprising: a first optical means for producing an output having a first state that corresponds to the first optical means being exposed to air and a second state that corresponds to the first optical means being exposed to fuel; second optical means for producing an output having a first state that corresponds to the second optical means being exposed to water, and a second state that corresponds to the second optical means being exposed to fuel; and circuit means for determining said first and second optical means output states.

2. The apparatus according to claim 1 wherein said first optical means comprises a first prism that receives light from a first light source and reflects light to a first light detector when the first prism is exposed to air, and said second optical means comprises a second prism that receives light from a second light source and reflects light to a second light detector when the second prism is exposed to water.

3. The apparatus according to claim 2 wherein said second prism exhibits total internal reflection when said prism is exposed to water in the form of ice buildup on said prism.

4. The apparatus of claim 3 wherein light is launched into said second prism with a wide angle beam to facilitate total internal reflection by reducing scattering when ice buildup occurs on said prism.

5. The apparatus of claim 4 wherein said beam spread angle is about 20° or more.

6. The apparatus of claim 2 wherein said first prism is disposed in a fuel tank so as to detect an air/fuel interface before said second prism detects an air/fuel interface.

7. The apparatus of claim 2 wherein said first prism has a conical contour and said second prism has a truncated conical contour.

8. The apparatus of claim 7 wherein said prisms comprise polyethersulfone.

9. The apparatus of claim 1 in combination with a fuel tank for detecting air/fuel/water interfaces at the bottom of the tank.

10. The apparatus of claim 9 wherein the fuel tank is an aircraft fuel tank.

11. The apparatus of claim 1 further comprising a sensor circuit connected to said first and second optical means for detecting said first and second optical means output states, said circuit means comprising a power source, said circuit means and power source being connected to said sensor circuit with a two wire electrical connection.

12. The apparatus of claim 11 wherein said circuit means determines said optical means output states based on said power source output current supplied to said sensor circuit.

13. The apparatus of claim 12 wherein said sensor circuit draws current at four discrete levels, each level respectively corresponding to air, water and fuel present conditions in the tank.

14. The apparatus of claim 13 wherein said first and second optical means each comprises a light source, a light detector and a prism, with each corresponding optical means output being based on internal reflection of light from its light source to its light detector.

15. The apparatus of claim 14 wherein said light detectors control operation of associated current load switches.

16. The apparatus of claim 15 wherein said light sources are LEDs that exhibit operating temperature variations that compensate temperature variations of said switches and light detectors.

17. The apparatus of claim 11 further comprising means for determining electrical open and short circuit conditions in said circuit means as part of a self-test capability.

18. An electronic circuit for determining the optical output state of a remote optical liquid level detector of the type having a light source, a prism and a light responsive switch that receives light reflected by the prism from the light source based on the interface between the prism and air or liquid, comprising: power source means for applying power to the light source, and means for detecting the light responsive switch state based on change in power drawn therefrom, said electronic circuit being connected to the optical detector by no more than two wires.

19. The electronic circuit according to claim 18 wherein said detecting means comprising a current sensing resistor in series between said power source and said optical liquid level detector, and means for detecting voltage drop across said resistor with said voltage drop corresponding to said light responsive switch state.

20. The electronic circuit of claim 19 further comprising means for performing a short/open circuit test of the circuit based on the current through said resistor.

21. An optical detector for discriminating between water and aircraft fuel in a fuel tank comprising: a prism disposed in the fuel tank, said prism having a frusto-conical tip that receives light from a light source and internally reflects light to a light detector when said tip is exposed to water, and refracts light into aircraft fuel when said tip is exposed to aircraft fuel.

22. The apparatus of claim 21 wherein said prism comprises polyethersulfone.

23. A method for liquid detection in a fuel tank, comprising the steps of:
 a. using a first prism to internally reflect light from a light source to a light detector when the prism is exposed to air, and refracting light away from the detector when the prism is exposed to fuel; and
 b. using a second prism to internally reflect light from a light source to a light detector when the second prism is exposed to water, and refracting light away from the detector when the second prism is exposed to fuel.

24. Apparatus for liquid detection in a fuel tank, comprising:

first optical means for internally reflecting light from a light source to a light detector when said first optical means is exposed to air, and refracting light away from the detector when said first optical means is exposed to fuel; and second optical means for internally reflecting light from a light source to a light detector when said second optical means is exposed to water, and refracting light away from the-detector when said second optical means is exposed to fuel.

25. An electronic circuit for determining the optical output state of a plurality of remote optical liquid level detectors, each detector being of the type having a light source, a prism and a light responsive switch that receives light reflected by the prism from the light source based on the interface between the prism and air or liquids, comprising: power source means for applying power to the light sources, and means for detecting the light receptor switches states based on change in power drawn therefrom, said electronic circuit being connected to the plurality of optical detectors by no more than two wires.

26. The circuit of claim 25 in combination with at least two optical detectors that are used to discriminate air, water and fuel interfaces with the prisms inside a fuel tank.

* * * * *